US008328052B2

(12) United States Patent
Hung

(10) Patent No.: US 8,328,052 B2
(45) Date of Patent: Dec. 11, 2012

(54) DISPENSING GUN

(75) Inventor: Hung Chih Hung, Changhua (TW)

(73) Assignee: Slang Syuan Fu Industry Co., Ltd., Homei, Changhua (TW)

( * ) Notice: Subject to any disclaimer, the term of this patent is extended or adjusted under 35 U.S.C. 154(b) by 125 days.

(21) Appl. No.: 13/065,434

(22) Filed: Mar. 22, 2011

(65) Prior Publication Data

US 2012/0145749 A1 Jun. 14, 2012

(30) Foreign Application Priority Data

Dec. 12, 2010 (TW) .............................. 99225815 U

(51) Int. Cl.

| | |
|---|---|
| ***B67D 7/60*** | (2010.01) |
| ***G01F 11/00*** | (2006.01) |
| ***B65D 88/54*** | (2006.01) |
| ***A61B 17/58*** | (2006.01) |
| ***A61B 17/60*** | (2006.01) |
| ***A61B 2/00*** | (2006.01) |
| *F16H 27/02* | (2006.01) |
| *F16H 31/00* | (2006.01) |

(52) U.S. Cl. .......... 222/391; 222/326; 74/141.5; 606/92

(58) Field of Classification Search .................. 222/391, 222/326, 327, 386, 309, 165; 684/183, 207–209; 606/92–93; 74/141.5, 522

See application file for complete search history.

(56) References Cited

U.S. PATENT DOCUMENTS

| | | | | |
|---|---|---|---|---|
| 2,305,238 | A * | 12/1942 | Coates | 74/169 |
| 2,582,156 | A * | 1/1952 | Peterson | 222/327 |
| 4,072,254 | A * | 2/1978 | Cox | 222/391 |
| 4,204,616 | A * | 5/1980 | Chang | 222/391 |
| 4,706,853 | A * | 11/1987 | Stonesifer et al. | 222/391 |
| 5,156,305 | A * | 10/1992 | Eyre | 222/327 |
| 5,197,635 | A * | 3/1993 | Chang | 222/137 |
| 5,381,931 | A | 1/1995 | Chang | |
| 5,626,263 | A | 5/1997 | Lii | |
| 5,720,418 | A * | 2/1998 | Timmerman et al. | 222/309 |
| 5,823,403 | A * | 10/1998 | Schneider | 222/391 |
| 6,155,463 | A * | 12/2000 | Dentler | 222/165 |
| 6,264,071 | B1 * | 7/2001 | Dentler | 222/391 |
| 2010/0237105 | A1 * | 9/2010 | Zagone | 222/391 |

* cited by examiner

*Primary Examiner* — Patricia Bianco
*Assistant Examiner* — Benjamin R Shaw
(74) *Attorney, Agent, or Firm* — Charles E. Baxley

(57) ABSTRACT

A dispensing gun includes a housing for holding a cartridge, a push rod engaged through the housing and having a plunger for engaging with the cartridge, an actuating plate engaged onto the push rod, a trigger pivotally secured to the housing and having an actuating pin for operating the actuating plate to move the push rod relative to the housing, a spring member biasing the actuating plate to engage with the actuating pin of the trigger, a latch engaged onto the push rod and biased to prevent the push rod from moving rearwardly relative to the housing when the actuating plate is released by the trigger, and a release member is located between the latch and the actuating pin of the trigger for being moved to release the push rod from the latch.

4 Claims, 3 Drawing Sheets

DISPENSING GUN

BACKGROUND OF THE INVENTION

1. Field of the Invention

The present invention relates to a dispensing gun, and more particularly to a dispensing gun including a pressure relieving device for suitably and effectively dispensing viscous materials, such as thick fluid or liquid, pasty materials, or mastic caulking materials, and for relieving the pressure of the viscous materials or the mastic caulking materials within the cartridge, and for preventing the viscous materials or the mastic caulking materials from moving out of the cartridge continuously after the required squeezing or dispensing operation.

2. Description of the Prior Art

Various kinds of typical dispensing guns have been developed and provided for dispensing various kinds of viscous materials, such as thick fluid or liquid, pasty materials, or mastic caulking materials which are retained in a cartridge that includes a discharge nozzle, and that includes an open end, and that includes a cup-shaped piston slidably received in the cartridge.

For example, U.S. Pat. No. 5,156,305 to Eyre, U.S. Pat. No. 5,381,931 to Chang, and U.S. Pat. No. 5,626,263 to Lii disclose several of the typical dispensing guns each comprising a rod slidably received in a supporting member and including a rack formed or provided therein, and a pair of pawls biased to engage with the rack with spring members for moving the rod forward step by step, and for forcing the piston to move forward and thus for forcing or squeezing the viscous materials or fluid out of the cartridge.

The pawls may only be used to force and to push the rod forward step by step, such that the viscous materials or fluid may be pressurized by the piston, and may be caused to move out of the cartridge continuously. Much of the viscous materials or fluid may thus be forced out of the cartridge continuously, and may be wasted and may not be used.

When the rod is moved rearwardly or backwardly by a release plate and an actuating handle or hand grip, a hollow compartment may be formed in the front end of the cartridge, next time, when the rod is forced to move forward by the actuating plate again, the piston may not be used to move or force any viscous materials or fluid out of the cartridge, the air received in the hollow compartment formed in the front end of the cartridge should be forced out of the cartridge before the viscous materials may be pressurized again by the piston. The actuating plate is thus required to be actuated many times before the required amount of mastic caulking materials or fluid may be forced or squeezed out of the cartridge.

However, when the hollow compartment is formed in the front end of the cartridge and when the rod is moved rearwardly or backwardly by the release plate, the air in the outer environment may be drawn into the cartridge, such that the mastic caulking materials may be easily hardened by the air. Furthermore, when the front end of the dispensing gun is directed upwardly or downwardly, the bush may not suitably engage with the release plate, and the rod thus may not be actuated or moved rearward by the release plate, such that the viscous materials may still be caused to move out of the cartridge continuously.

The present invention has arisen to mitigate and/or obviate the afore-described disadvantages of the conventional mechanisms for the dispensing guns.

SUMMARY OF THE INVENTION

The primary objective of the present invention is to provide a dispensing gun including a pressure relieving device for suitably and effectively dispensing viscous materials, such as thick fluid or liquid, pasty materials, or mastic caulking materials, and for relieving the pressure of the viscous materials or the mastic caulking materials within the cartridge, and for preventing the viscous materials or the mastic caulking materials from moving out of the cartridge continuously after the required squeezing or dispensing operation.

The other objective of the present invention is to provide a dispensing gun including a pressure relieving device for preventing the air from flowing into the cartridge and for preventing the viscous materials or the mastic caulking materials or the fluid from being hardened by the air.

In accordance with one aspect of the invention, there is provided a dispensing gun comprising a housing including a handle extended therefrom, and including a chamber formed therein, and including an aperture formed therein and communicative with the chamber of the housing, and including a cylindrical member having a compartment formed therein for engaging with and for holding a cartridge therein, a push rod slidably engaged through the aperture of the housing, and including a first end having a plunger provided thereon for engaging with a piston of the cartridge, an actuating plate including an orifice formed therein for receiving the push rod, a trigger pivotally secured to the housing and having an actuating pin for engaging with the actuating plate and for operating the actuating plate to move the push rod forwardly relative to the housing and for forcing a viscous material out of the cartridge, a first spring member engaged with the actuating plate for biasing the actuating plate to engage with the actuating pin of the trigger, a latch including a hole formed therein for receiving the push rod, a second spring member engaged with the latch for tilting the latch relative to the push rod and for actuating the latch to engage and to grasp the push rod and for preventing the push rod from moving rearwardly relative to the latch and the housing when the actuating plate is released by the trigger and for limiting a rearward movement of the push rod relative to the housing, and a release member slidably engaged in the housing and located between the latch and the actuating pin of the trigger for being selectively actuated and moved by the actuating pin of the trigger to engage with the latch and to erect the latch relative to the push rod and to selectively release the push rod from the latch.

The housing includes a retaining member for engaging with the latch and for positioning the latch relative to the housing. The retaining member is an L-shaped member attached to a rear portion of the housing.

The housing includes a positioning member engaged in the housing and extended into the chamber of the housing for selectively engaging with the actuating plate and for allowing the actuating plate to be erected and perpendicular to the push rod.

Further objectives and advantages of the present invention will become apparent from a careful reading of the detailed description provided hereinbelow, with appropriate reference to the accompanying drawings.

DETAILED DESCRIPTION OF THE PREFERRED EMBODIMENT

Figure 1:
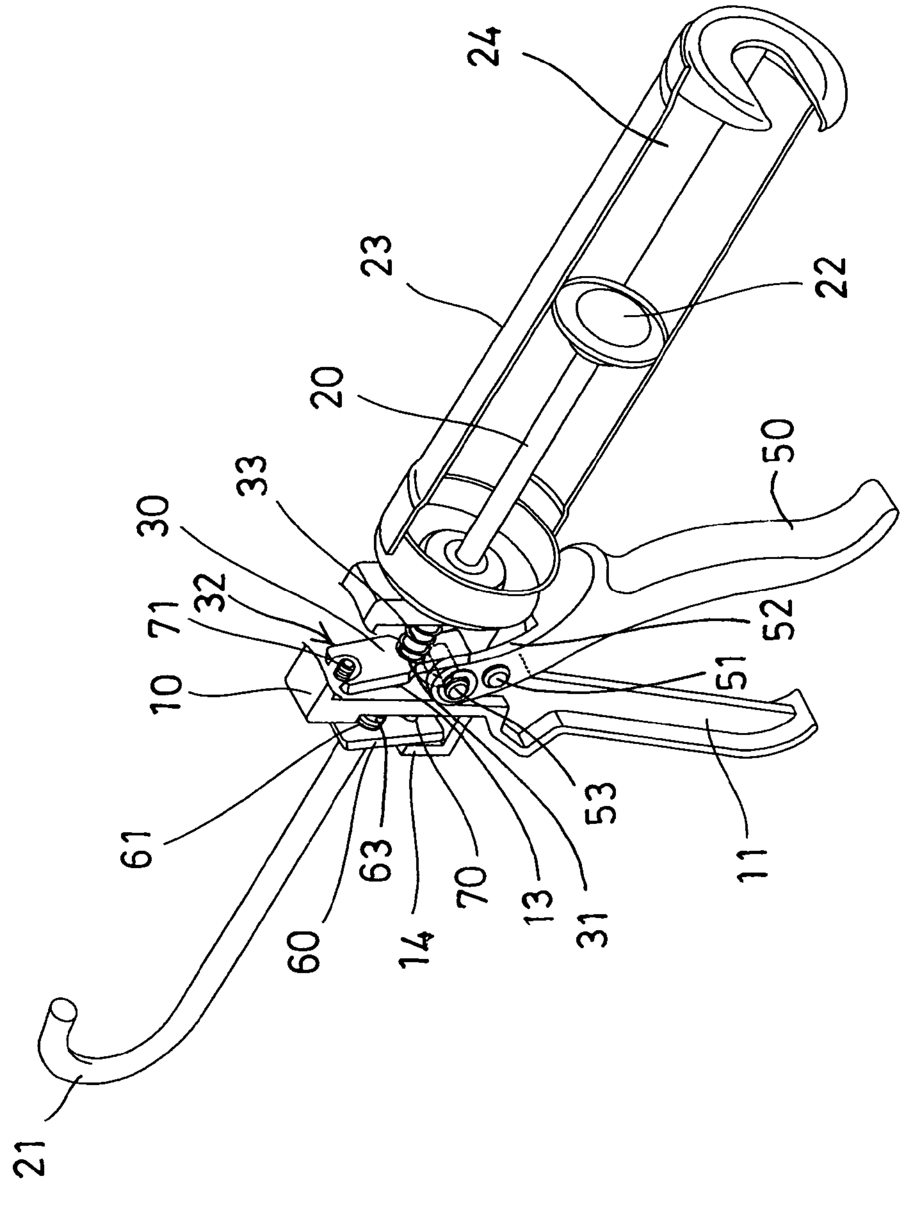
FIG. 1 is a perspective view of a dispensing gun in accordance with the present invention.
Figure 2:
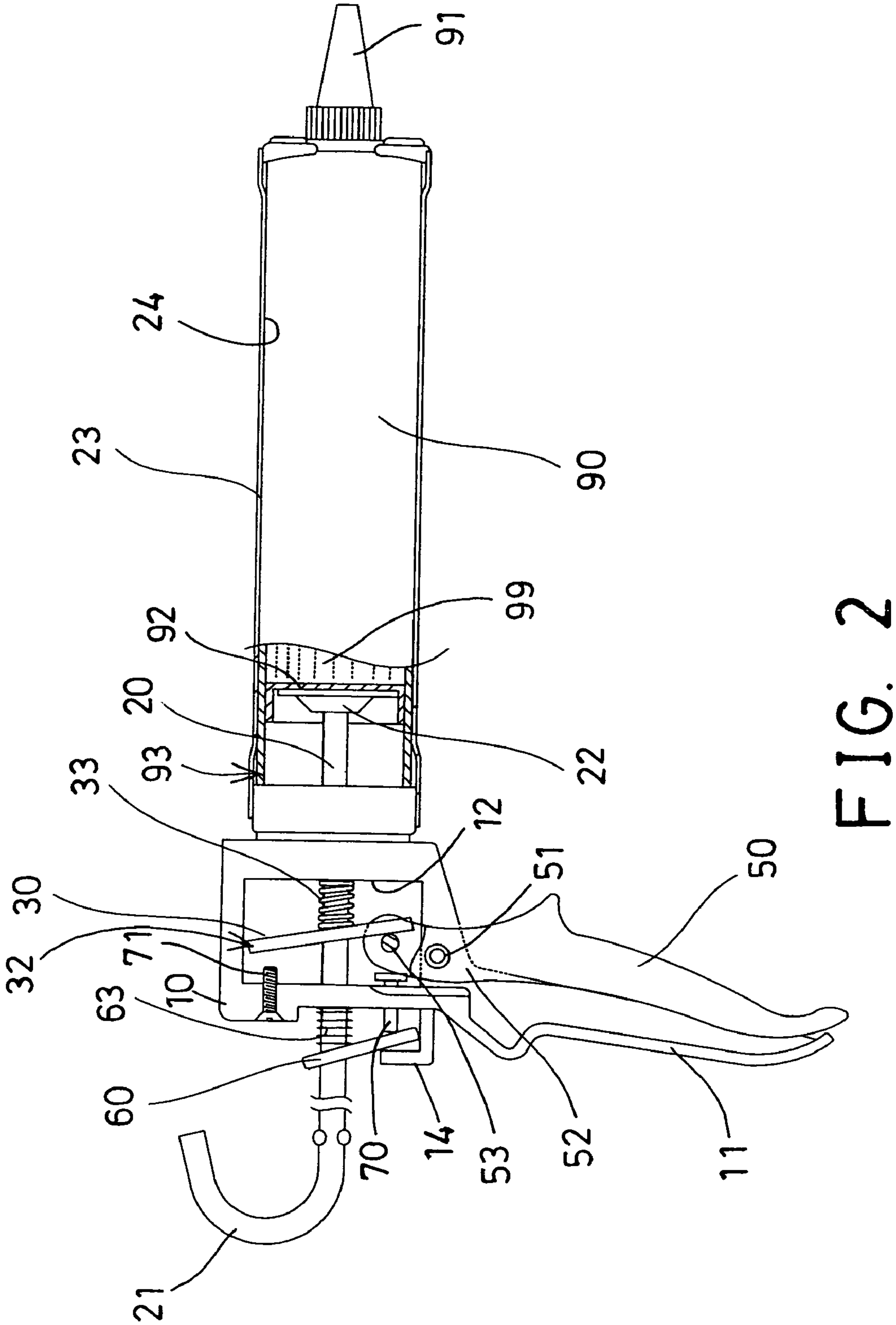
FIG. 2 is a side plan schematic view of the dispensing gun, in which a portion of the outer housing or cartridge has been cut off for showing the inner structure of the outer housing or cartridge.

Referring to the drawings, and initially to FIGS. 1 and 2, a dispensing gun in accordance with the present invention comprises a stock or housing 10 including a handle 11 extended downwardly and generally, but not necessarily perpendicularly to the longitudinal direction of the housing 10, and including a chamber 12 formed therein, such as formed in the middle portion of the housing 10, and including an aperture 13 (FIG. 1) laterally formed therein and intersecting or communicative with the chamber 12 of the housing 10. The housing 10 includes an L-shaped retainer or anchoring or supporting or retaining member 14 formed thereon or attached or mounted or extended rearwardly or laterally from the lower or rear portion thereof.

A push rod 20 is slidably engaged in the aperture 13 of the housing 10 and movable forwardly and rearwardly relative to the housing 10, and includes a curved hand grip 21 provided or extended on the rear portion of the push rod 20, in which the push rod 20 may be moved longitudinally or forwardly and rearwardly relative to the housing 10 with the hand grip 21, and includes a plunger 22 attached to the front end thereof. A frame or barrel or cylindrical member 23 is disposed or attached or mounted or secured to or extended from the front portion of the housing 10, and includes a compartment 24 formed therein for receiving or holding and engaging with a cartridge 90 therein (FIGS. 2-3).

Figure 3:
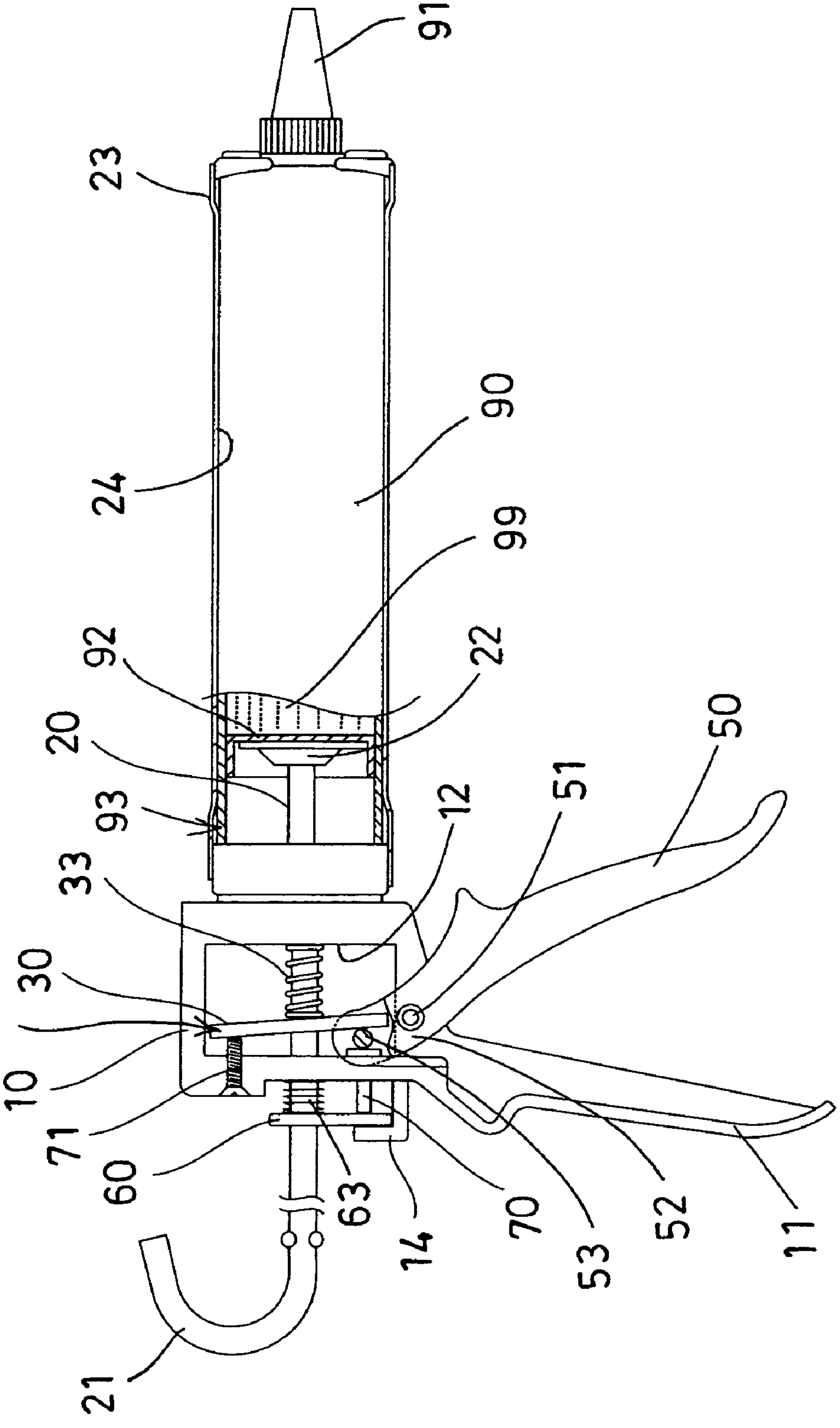
FIG. 3 is another side plan schematic view similar to FIG. 2, illustrating the operation of the dispensing gun.

The cartridge 90, as shown in FIGS. 2-3, includes a generally cylindrical shape for receiving or holding or containing various kinds of viscous material 99 or fluid therein, such as a caulking mastic, and includes a nozzle 91 formed or provided on the front portion of the cylindrical cartridge 90, and includes an open rear end 93, and includes a free cup-shaped piston 92 slidably received in the open rear end 93 thereof and slidable or movable along or relative to the cartridge 90. The plunger 22 of the push rod 20 may be engaged with the piston 92 of the cartridge 90 for moving the piston 92 along the cartridge 90 and for moving or forcing or squeezing the viscous material 99 out of the nozzle 91 of the cartridge 90, when required.

An actuating plate 30 includes an orifice 31 formed therein (FIG. 1) and having an area slightly greater than that of the push rod 20 for allowing the push rod 20 to be slidably received or engaged in the aperture 31 of the actuating plate 30, and for allowing the push rod 20 to be frictionally engaged with the actuating plate 30 when the actuating plate 30 is disposed or arranged or tilted relative to the push rod 20. A trigger 50 includes an upper portion rotatably or pivotally secured to the housing 10 or the handle 11 with a spindle or pivot axle 51, and includes an actuating upper portion formed or defined by a pair of flaps 52, and includes an actuating pin 53 disposed or attached or mounted or secured in the actuating upper portion thereof and bridged between the flaps 52.

A compression spring member 33 is engaged around the push rod 20 and received or contained in the chamber 12 of the housing 10, and engaged between the actuating plate 30 and the housing 10 for forcing or biasing the actuating plate 30 leftwardly or rearwardly to engage with the actuating pin 53 of the trigger 50. In operation, the actuating plate 30 may be tilted or inclined relative to the push rod 20 by the actuating pin 53 of the trigger 50 and thus may be caused or forced to engage and hold or grasp the push rod 20, in order to move the push rod 20 forward incrementally when the lower portion of the actuating plate 30 is forced or actuated to move forward step by step by the actuating pin 53 of the trigger 50.

The actuating plate 30 may be moved or biased rearwardly and toward the actuating pin 53 of the trigger 50 by the spring member 33 and may release the actuating plate 30 from the push rod 20, and thus the trigger 50 may be moved away from the handle 11 by the spring member 33 and the actuating plate 30 when the trigger 50 is released. However, it is to be noted that the actuating plate 30 will be biased and moved to a position substantially perpendicular to the push rod 20 by the spring member 33 when the trigger 50 is released such that the push rod 20 may also be released, and the push rod 20 may then be moved forward incrementally when the actuating plate 30 is moved forward by the actuating pin 53 of the trigger 50 again, the push rod 20 may no longer be moved forwardly by the actuating plate 30 and the actuating pin 53 of the trigger 50 when the actuating plate 30 is moved rearwardly by the spring member 33.

An anchor or latch 60 includes a hole 61 formed therein (FIG. 1) for loosely receiving the push rod 20, and the latch 60 is loosely held in relation to the housing 10 by the retaining member 14 that is laterally extended or projected from the rear portion of the housing 10 and that may be used to position the latch 60 relative to the housing 10. Another spring member 63 is engaged on or around the push rod 20 and biased or engaged between the housing 10 and the latch 60 for biasing the latch 60 rearwardly or toward and to engage with the laterally extended retaining member 14 of the housing 10 and for tilting the latch 60 relative to the push rod 20 and thus to engage and grasp the push rod 20 for preventing the push rod 20 from moving rearwardly relative to the latch 60 and the housing 10 when the actuating plate 30 is released by the trigger 50. The latch 60 may thus act as a device for limiting the push rod 20 to move rearwardly relative to the housing 10 and the cartridge 90.

A release rod or member 70 is laterally and slidably received or engaged in the upper and rear portion of the housing 10 and disposed or arranged substantially parallel to the push rod 20, and disposed or arranged or located between the latch 60 and the actuating pin 53 of the trigger 50 for being selectively actuated or operated or moved by the actuating pin 53 of the trigger 50 to engage with the latch 60 (FIG. 3). In operation, as shown in FIG. 2, when the release member 70 is not actuated or pushed by the actuating pin 53 of the trigger 50, the latch 60 may be tilted or inclined relative to the push rod 20 and to engage and grasp the push rod 20 and to prevent the push rod 20 from moving rearwardly relative to the latch 60 and the housing 10 when the actuating plate 30 is released by the trigger 50.

However, as shown in FIG. 3, when the release member 70 is actuated or pushed rearwardly to engage with the latch 60 by the actuating pin 53 of the trigger 50, the latch 60 may be moved and erected relative to the push rod 20 to a position perpendicular to the push rod 20 such that the push rod 20 may be released relative to the latch 60, and the push rod 20 may then be moved rearwardly and away from the cartridge 90. It is preferable that the housing 10 further includes a positioning member 71 engaged in the upper portion of the housing 10 and extended into the chamber 12 of the housing 10 for selectively engaging with the upper portion 32 of the actuating plate 30 (FIG. 3). It is to be noted that, as shown in FIG. 1, a portion of the upper portion 32 of the actuating plate 30 has been cut off for showing the positioning member 71, actually, the positioning member 71 may be selectively engaged with the upper portion 32 of the actuating plate 30.

In operation, as shown in FIG. 2, when the push rod 20 is moved forwardly and incrementally by the actuating plate 30 and the trigger 50, the plunger 22 and the piston 92 may be moved forwardly in order to squeeze the viscous materials 99 out through the nozzle 91 of the cartridge 90. At this moment, the latch 60 may be moved and tilted rearwardly relative to the push rod 20 by the spring member 63 in order to engage and grasp the push rod 20 and to prevent the push rod 20 from moving rearwardly relative to the latch 60 and the housing 10 when the actuating plate 30 is released by the trigger 50. The actuating plate 30 and the trigger 50 may act as an actuating or moving device for moving the push rod 20 forwardly relative to the housing 10 and the cartridge 90.

When the trigger 50 is released, the actuating plate 30 may also be moved or biased leftwardly or rearwardly by the spring 33 and thus may also be released. When the actuating pin 53 is further moved leftwardly or rearwardly to engage with the release member 70 and to actuate or push or move the release member 70 to engage with the latch 60 (FIG. 3), the latch 60 may be moved and erected relative to the push rod 20 to a position perpendicular to the push rod 20 such that the push rod 20 may be released relative to the latch 60, and the push rod 20 may then be moved rearwardly and away from the cartridge 90 with the curved hand grip 21 when required. The upper portion 32 of the actuating plate 30 may be selectively engaged with the positioning member 71 for allowing the actuating plate 30 to be moved to a position substantially perpendicular to the push rod 20.

Accordingly, the dispensing gun in accordance with the present invention includes a pressure relieving device for suitably and effectively dispensing viscous materials, such as thick fluid or liquid, pasty materials, or mastic caulking materials, and for relieving the pressure of the viscous materials or the mastic caulking materials within the cartridge, and for preventing the viscous materials or the mastic caulking materials from moving out of the cartridge continuously after the required squeezing or dispensing operation.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A dispensing gun comprising:

a housing including a handle extended therefrom, and including a chamber formed therein, and including an aperture formed therein and communicative with the chamber of the housing, and including a cylindrical member having a compartment formed therein for engaging with and for holding a cartridge therein, a push rod slidably engaged through said aperture of said housing, and including a first end having a plunger provided thereon for engaging with a piston of the cartridge, an actuating plate including an orifice formed therein for receiving said push rod, a trigger pivotally secured to said housing and having an actuating pin for engaging with said actuating plate and for operating said actuating plate to move said push rod forwardly relative to said housing and for forcing a viscous material out of the cartridge, a first spring member engaged with said actuating plate for biasing said actuating plate to engage with said actuating pin of said trigger, a latch including a hole formed therein for receiving said push rod, a second spring member engaged with said latch for tilting said latch relative to said push rod and for actuating said latch to engage and to grasp said push rod and for preventing said push rod from moving rearwardly relative to said latch and said housing when said actuating plate is released by said trigger and for limiting a rearward movement of said push rod relative to said housing, and a release member slidably engaged in said housing and located between said latch and said actuating pin of said trigger for being selectively actuated and moved by said actuating pin of said trigger to engage with said latch and to erect said latch relative to said push rod and to selectively release said push rod from said latch.

2. The dispensing gun as claimed in claim 1, wherein said housing includes a retaining member for engaging with said latch and for positioning said latch relative to said housing.

3. The dispensing gun as claimed in claim 2, wherein said retaining member is an L-shaped member attached to a rear portion of said housing.

4. The dispensing gun as claimed in claim 1, wherein said housing includes a positioning member engaged in said housing and extended into said chamber of said housing for selectively engaging with said actuating plate.

* * * * *